(12) United States Patent
Yasuda et al.

(10) Patent No.: US 6,563,329 B2
(45) Date of Patent: May 13, 2003

(54) SENSOR FOR MEASURING RESISTIVITY

(75) Inventors: Yoshimichi Yasuda, Tokyo (JP); Seiji Kamesaka, Tokyo (JP)

(73) Assignee: Kabushiki Kaisha Saginomiya Seisakusho, Tokyo (JP)

( * ) Notice: Subject to any disclaimer, the term of this patent is extended or adjusted under 35 U.S.C. 154(b) by 109 days.

(21) Appl. No.: 09/779,178

(22) Filed: Feb. 8, 2001

(65) Prior Publication Data

US 2002/0105345 A1 Aug. 8, 2002

(51) Int. Cl.[7] .............................................. C01R 27/08
(52) U.S. Cl. ........................................ 324/691; 324/515
(58) Field of Search ................................. 324/691, 444, 324/515; 420/582, 584, 586; 437/10

(56) References Cited

U.S. PATENT DOCUMENTS

| | | | | |
|---|---|---|---|---|
| 4,487,744 A | * | 12/1984 | DeBold et al. | 420/584 |
| 4,820,650 A | * | 4/1989 | Nagae et al. | 437/10 |
| 4,911,886 A | * | 3/1990 | Pitler et al. | 420/586 |
| 5,011,659 A | * | 4/1991 | Culling | 420/582 |
| 5,945,067 A | * | 8/1999 | Hibner et al. | 420/586 |

FOREIGN PATENT DOCUMENTS

JP  02000046773 A  *  2/2000  .......... G01N/27/07

* cited by examiner

Primary Examiner—Christine Oda
Assistant Examiner—Walter Benson
(74) Attorney, Agent, or Firm—Butzel Long

(57) ABSTRACT

A sensor for measuring resistivity having metallic electrode members with excellent resistance to corrosion and oxidation is provided. The metallic electrode member for measuring resistivity of liquid consists of nickel-based alloy containing 19 to 24 wt % of chromium and 1 to 7 wt % of iron. The sensor for measuring resistivity enables stable measurement of the resistivity over a long period of time with simple maintenance.

5 Claims, 1 Drawing Sheet

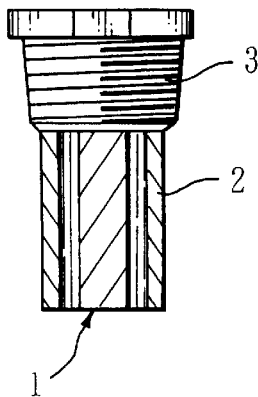
F I G. 1
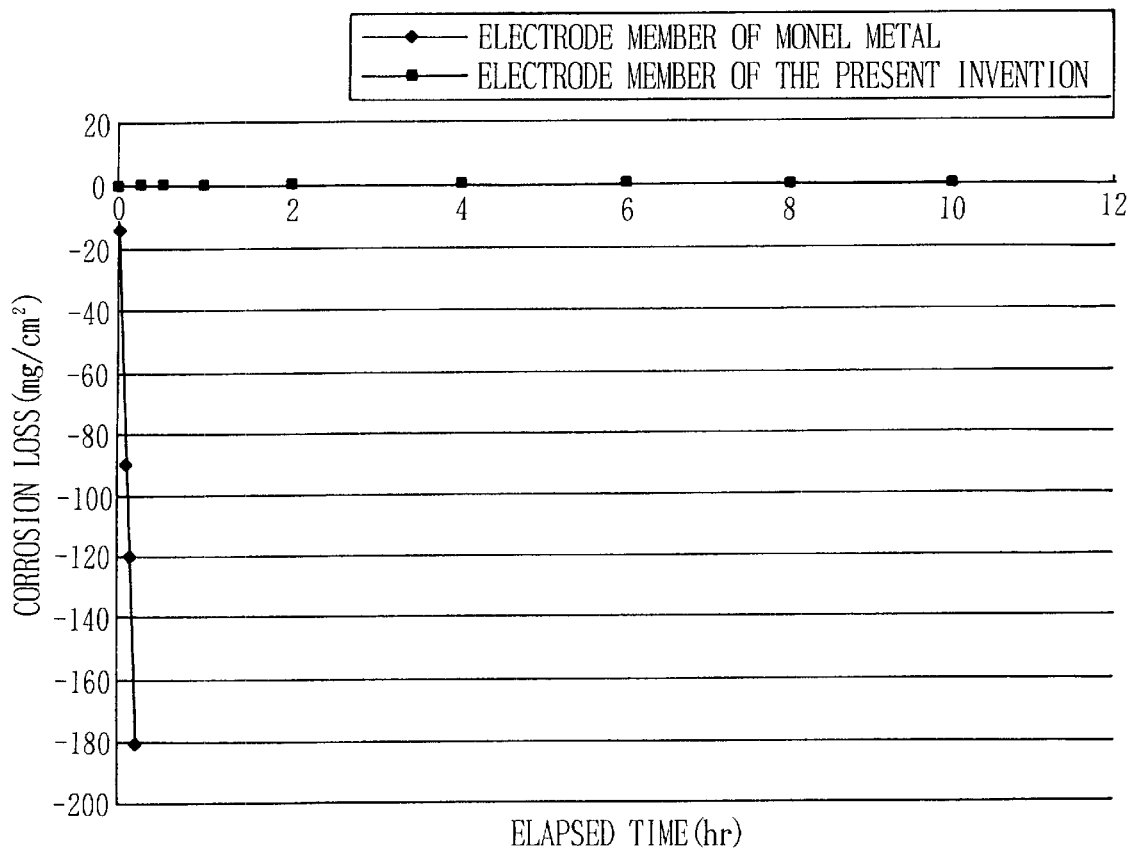
F I G. 2

SENSOR FOR MEASURING RESISTIVITY

BACKGROUND OF THE INVENTION (1) Field of the Invention

This invention relates to a sensor for measuring resistivity of ultrapure water used mainly for cleaning semiconductor wafers and, more specifically, to the composition of an alloy, with the aid of which the resistance to corrosion and oxidation of a metallic electrode member is improved.

(2) Description of the Related Art

In a process for manufacturing semiconductor wafers, even very fine dust or a little dirt is not allowed to get in, therefore a very severe cleaning of the wafers is required. A cleaning by using chemicals and ultrapure water has been employed as a method of the cleaning. That is, in a cleaning process of semiconductor wafers, surfaces of the semiconductor wafers are cleaned with various chemicals such as a mixed solution of dilute hydrochloric acid with hydrogen peroxide water and dilute hydrofluoric acid, and then the chemicals adhering to the surface of the wafer are cleaned off by using ultrapure water.

In the method of the cleaning described above, generally, the electrical resistivity of spent ultrapure water is measured so as to judge whether the chemicals are cleaned off from the surface of the wafer or not, and in this resistivity measurement a sensor for measuring resistivity having metallic electrode members has been used. As to the sensor, a pair of electrodes arranged facing with each other is immersed into a liquid to be measured, an alternating voltage is applied between both electrodes to detect a change in current flowing between the electrodes, thereby an electrical resistance of the liquid to be measured is measured.

In the cleaning process described above, the cleaning with ultrapure water may be carried out in the same tank, which has been used for the cleaning with the chemicals, and in such a case, when the chemicals are replaced by the ultrapure water, the electrode member described above may be exposed to the chemicals. Therefore, a metal such as titanium (Ti), stainless steel, Monel metal and platinum (Pt) is known as the electrode member.

Among electrode members consisting of the metal described above, when titanum is employed as the electrode, the titanium electrode is corroded by dilute hydrofluoric acid, the oxidation resistance deteriorates, the surface of the titanium electrode is oxidized during use and a film having significantly high electrical resistance is formed on the surface, in which the thickness of the film changes with time passing, the electrode property easily changes with a disturbance such as a temperature change, thereby causing a problem in the reliability as the electrode.

When stainless steel is employed as the electrode, stainless steel has poor resistance to acid, though a degree of the change with time passing is less compared to the titanium electrode, an increase in resistivity with time passing due to the oxidation of the surface of the electrode is inevitable, thereby the deterioration in the reliability during use for a long period of time is inevitable.

When Monel metal is employed as the electrode, Monel meral has poor resistance to acid, and when the chemical for cleaning containing dilute hydrochloric acid is used, the Monel metal electrode cannot be used for a long period of time.

To the contrary, since platinum is chemically very stable metal, the platinum electrode has no problem in terms of the performance and is very useful in a laboratory scale, however the platinum electrode is not feasible in a practical use because of its high cost.

A resistivity meter, in which Monel metal containing no chromium is used, is commercially available for use in cleaning with the chemical containing dilute hydrochloric acid. However, the resistivity meter is corroded by a cleaning fluid consisting of hydrochloric acid, hydrogen peroxide water and water, which is used for cleaning semiconductors, therefore the resistivity meter cannot be used for a process of cleaning semiconductors.

SUMMARY OF THE INVENTION

It is therefore an objective of the present invention to solve the above problem and to provide a metallic electrode member having excellent resistance to corrosion and oxidation, thereby providing a sensor for measuring resistivity, which enables stable measurement of the resistivity over a long period of time with simple maintenance.

In order to attain the above objective, the present invention is to provide a sensor for measuring resistivity having metallic electrode members for measuring resistivity of liquid, characterized in that the metallic electrode member consists of nickel-based alloy containing 19 to 24 wt % of chromium and 1 to 7 wt % of iron. According to the composition described above, the resistance to corrosion and oxidation of the electrode is significantly improved.

BRIEF DESCRIPTION OF THE DRAWINGS

FIG. 1 is a sectional view of a sensor for measuring resistivity according to the present invention; and FIG. 2 is a chart illustrating the aging of corrosion loss, in which the corrosion resistance of an electrode member according to the present invention is compared with that of a conventional electrode member.

DESCRIPTION OF THE PREFERRED EMBODIMENTS

In the following, the preferred embodiments of the present invention will be explained in detail. As shown in FIG. 1, a sensor for measuring resistivity according to the present invention includes an inner electrode 1 as a central electrode and a cylindrical outer electrode 2, which concentrically surrounds the inner electrode 1 leaving a space therebetween, wherein the inner electrode 1 and the outer electrode 2 are held by a nipple 3.

An alloy consituting the electrode member used in the present invention is a nickel-based alloy, to which 19 to 24 wt % (hereinafter, % denoting wt %, unless otherwise specified) of chromium and 1 to 7% of iron are added to have the resistance to acid and base, thereby improving the resistance to oxidation and acid as well as the mechanical strength of the electrode. The addition of chromium is effective for improving the oxidation resistance, especially for improving that at an elevated temperature, and if the content of chromium is less than 19%, the effect of improving oxidation resistance is hard to expect, on the other hand when more than 24%, an adverse effect takes place.

The nipple 3 may consist of the same alloy with that constituting the electrode member, thereby preventing a leak of ultrapure water and so on, which might occur because of corrosion.

In the following, examples of the present invention will be explained.

EXAMPLE 1

An electrode member for measuring resistivity consisting of nickel-based alloy, containing 22% of chromium, 13% of molybdenum, 3% of tungsten, 4% of iron and the balance essentially consisting of nickel, was prepared. As an accelerated examination, four test pieces thus made of the nickel-based alloy were immersed into a dilute hydrochloric acid kept at 85° C. and the corrosion loss was measured. Although in a practical cleaning process of semiconductor wafers, an electrode member for measuring resistivity is not exposed to an acid and oxidation atmosphere such as the dilute hydrochloric acid described above, the accelerated examination consisting of the immersion for a long period of time was carried out.

A result of the accelerated examination is shown in FIG. 2, in which the corrosion loss (mg/cm$^2$) and the immersion time (hr), i.e. the elapsed time from the start of the immersion, are shown with the longitudinal and transverse axes, respectively. As apparent from FIG. 2, for the electrode made of the above nickel-based alloy, no significant corrosion loss was observed after a lapse of 12 hours from the start of the immersion. Since there was no significant difference in values of the corrosion loss for the four test pieces, the data of the corrosion loss is shown as a point for each observed immersion time in FIG. 2.

As apparent from FIG. 2, for the electrode made of the above nickel-based alloy, no significant corrosion loss was observed for a long period of time in the acid and oxidation atmosphere, revealing that this electrode ensured a stable performance for a long period of time. No significant change was observed for the surface of every immersed test piece and an excellent resistane to corrosion and oxidation was confirmed from the surface characteristic.

EXAMPLE 2

An electrode member for measuring resistivity consisting of nickel-based alloy, containing 19% of chromium, 16% of molybdenum, 4% of tungsten, 4% of iron and the balance essentially consisting of nickel, was prepared. Test pieces thereof were immersed into a dilute hydrochloric acid similar to that in the Example 1 and the corrosion loss was measured.

As to the electrode made of the above nickel-based alloy, no significant corrosion loss was observed for a long period of time in the acid and oxidation atmosphere, revealing that this electrode ensured a stable performance for a long period of time.

EXAMPLE 3

An electrode member for measuring resistivity consisting of nickel-based alloy, containing 24% of chromium, 7% of iron and the balance essentially consisting of nickel, was prepared. Test pieces thereof were immersed into a dilute hydrochloric acid similar to that in the Example 1 and the corrosion loss was measured.

The electrode made of the above nickel-based alloy showed a particularly excellent resistance to acid.

EXAMPLE 4

An electrode member for measuring resistivity consisting of nickel-based alloy, containing 20% of chromium, 5% of iron and the balance essentially consisting of nickel, was prepared.

Test pieces thereof were immersed into a dilute hydrochloric acid similar to that in the Example 1 and the corrosion loss was measured.

The electrode made of the above nickel-based alloy showed a good resistance to corrosion and oxidation.

COMPARATIVE EXAMPLE 1

Test pieces made of Monel metal, which has been employed as a conventional electrode member and is a nickel-copper alloy consisting of 66.5% of nickel and the balance essentially consisting of copper, were immersed into a dilute hydrochloric acid kept at 85° C. and the corrosion loss was measured. Although in a practical cleaning process of semiconductor wafers, an electrode member for measuring resistivity is not exposed to an acid and oxidation atmosphere such as the dilute hydrochloric acid described above, the accelerated examination consisting of the immersion for a long period of time was carried out.

A result of the above accelerated examination is shown in FIG. 2, in which the corrosion loss (mg/cm$^2$) and the immersion time (hr), i.e. the elapsed time from the start of the immersion, are shown with the longitudinal and transverse axes, respectively. As apparent from FIG. 2, for the conventional electrode made of the Monel metal, a corrosion loss of 180 mg/cm$^2$ was observed after a lapse of 15 minutes from the start of the immersion.

COMPARATIVE EXAMPLE 2

An electrode member for measuring resistivity consisting of nickel-based alloy, containing 22% of chromium, 6.5% of molybdenum, 3% of tungsten, 19.5% of iron and the balance essentially consisting of nickel, was prepared. Test pieces thereof were immersed into a dilute hydrochloric acid kept at 85° C. similar to that in the Example 1 and the corrosion loss was measured.

Although the above test pieces had a good corrosion resistance against sulfuric acid or phosphoric acid at high temperature, they showed a local corrosion against the dilute hydrochloric acid described above.

COMPARATIVE EXAMPLE 3

An electrode member for measuring resistivity consisting of nickel-based alloy, containing 30% of chromium, 5% of molybdenum, 2.5% of tungsten, 15% of iron and the balance essentially consisting of nickel, was prepared. Test pieces thereof were immersed into a dilute hydrochloric acid kept at 85° C. similar to that in the Example 1 and the corrosion loss was measured.

Although the above test pieces had a good corrosion resistance against phosphoric acid or acids having strong oxidizing property, they showed a local corrosion against the dilute hydrochloric acid described above.

Since the electrode member according to the present invention has an excellent resistance to corrosion and oxidation, the use thereof is not limited to the use for measuring resistivity of ultrapure water in the cleaning process of semiconductor wafers, but can be a use as a sensor for measuring resistivity in various chemical plant, food production plant and water treatment plant.

As apparent from the aforementioned explanation, according to the electrode member of the present invention, the resistance to corrosion and oxidation is significantly improved compared to a conventional electrode consisting of Monel metal, and a stable performace can be maintained for a long period of time as an electrode member for a sensor for measuring resistivity. Consequently, in a cleaning process of semiconductor wafers, a stable control of cleaning can be attained, the control of electrode characteristics and replacement of electrode are not required for a long period of time, and the cost down for the cleaning process can be attained.

The nipple, which holds the inner and outer electrodes, consists of the same alloy with that constituting the electrode member, thereby preventing a leak of ultrapure water and so on, which might occur because of corrosion.

A use of the sensor for measuring resistivity according to the present invention is not limited to the use for measuring resistivity of ultrapure water in the cleaning process of semiconductor wafers, but can be a use for a sensor for measuring resistivity in other various plant, and in such an industrial field, time and labor required for controlling the electrode characteristics and the replacement of electrode can be significantly decreased, thereby the cost down can be attained.

What is claimed is:

1. A sensor for measuring resistivity which comprises a metallic electrode member for measuring resistivity of liquid, the metallic electrode member consists of nickel-based alloy containing 19 to 24 wt % chromium and 1 to 7 wt % iron.

2. The sensor for measuring resistivity according to claim 1, wherein the metallic electrode member consists of 20 to 23 wt % chromium, 12 to 15 wt % molybdenum, 2 to 4 wt % tungsten, 2 to 6 wt % iron and the balance essentially consisting of nickel.

3. The sensor for measuring resistivity according to claim 1, wherein the Sensor for measuring resistivity measures resistivity of ultrapure water for use in a process for cleaning semiconductor wafers.

4. The sensor for measuring resistivity according to claim 2, wherein the sensor for measuring resistivity measures resistivity of ultrapure water for use in a process for cleaning semiconductor wafers.

5. The sensor for measuring resistivity as claimed in any one of claims 1 to 4, wherein a nipple is provided for holding the sensor for measuring resistivity, the nipple containing 19 to 24 wt % chromium and 1 to 7 wt % iron.

* * * * *